United States Patent
Philippon et al.

(10) Patent No.: US 9,931,288 B2
(45) Date of Patent: Apr. 3, 2018

(54) COMPOSITION COMPRISING AN AQUEOUS MEDIUM

(71) Applicant: L'OREAL, Paris (FR)

(72) Inventors: Céline Philippon, L'hay les Roses (FR); Géraldine Lerebour, Les Loges (FR); Catherine Marion, Antony (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/101,660

(22) PCT Filed: Dec. 2, 2014

(86) PCT No.: PCT/EP2014/076191
§ 371 (c)(1),
(2) Date: Jun. 3, 2016

(87) PCT Pub. No.: WO2015/082443
PCT Pub. Date: Jun. 11, 2015

(65) Prior Publication Data
US 2016/0303017 A1    Oct. 20, 2016

(30) Foreign Application Priority Data

Dec. 3, 2013 (FR) ...................... 13 61975

(51) Int. Cl.
| | |
|---|---|
| *A61K 8/02* | (2006.01) |
| *A61K 8/34* | (2006.01) |
| *A61K 8/44* | (2006.01) |
| *A61K 8/60* | (2006.01) |
| *A61Q 1/14* | (2006.01) |
| *A61Q 19/00* | (2006.01) |
| *A61Q 19/10* | (2006.01) |
| *C11D 1/90* | (2006.01) |
| *C11D 3/22* | (2006.01) |

(52) U.S. Cl.
CPC .............. *A61K 8/44* (2013.01); *A61K 8/0208* (2013.01); *A61K 8/0216* (2013.01); *A61K 8/345* (2013.01); *A61K 8/442* (2013.01); *A61K 8/60* (2013.01); *A61Q 1/14* (2013.01); *A61Q 19/00* (2013.01); *A61Q 19/10* (2013.01); *A61K 2800/30* (2013.01); *A61K 2800/49* (2013.01); *A61K 2800/524* (2013.01)

(58) Field of Classification Search
CPC . A61K 8/02; A61K 8/34; A61K 8/345; A61K 8/44; A61K 8/60; A61Q 1/14; A61Q 19/00; A61Q 19/10; C11D 1/662; C11D 1/90; C11D 3/2041; C11D 3/22
See application file for complete search history.

(56) References Cited

FOREIGN PATENT DOCUMENTS

| FR | 2-966-726 A1 | 5/2012 |
|---|---|---|
| WO | WO-2013-167220 A1 | 11/2013 |

OTHER PUBLICATIONS

Mintel, "Daily Purifying Facial Scrub" Product Literature, pp. 1-2, Dec. 2007.*
Database GNPD [Online] Mintel; Jul. 2012; "Cleaning Gel"; XP002729515.
Database GNPD [Online] Mintel; Dec. 2007; "Purifying Facial Scrub"; XP002729516.
Database GNPD [Online] Mintel; Jun. 2013; "Instant Revitalizing Shower Gel—Body & Hair"; XP002729517.
Database GNPD [Online] Mintel; Sep. 2013; "The Cleaning Gel"; XP002729518.

* cited by examiner

*Primary Examiner* — Brian P Mruk
(74) *Attorney, Agent, or Firm* — Polsinelli PC

(57) ABSTRACT

The present invention relates to a composition comprising, in a physiologically acceptable aqueous medium, at least one monosaccharide or a polysaccharide containing up to six sugar units, a polyol and a betaine, said composition being free of potassium sorbate. According to a preferred embodiment of the invention, the composition comprises sucrose, 1,3-propanediol and cocoyl betaine, said composition being free of potassium sorbate. The invention also relates to an article comprising such a composition, and also to a cosmetic process for treating keratin materials by applying such a composition and/or such an article.

21 Claims, No Drawings

COMPOSITION COMPRISING AN AQUEOUS MEDIUM

CROSS REFERENCE TO RELATED APPLICATIONS

This application is a National Phase filing under 35 U.S.C. § 371 of PCT/EP2014/076191 filed on Dec. 2, 2014; and this application claims priority to Application No. 1361975 filed in France on Dec. 3, 2013 under 35 U.S.C. § 119. The entire contents of each application are hereby incorporated by reference.

The invention relates to a composition comprising, in a physiologically acceptable aqueous medium, at least one monosaccharide or a polysaccharide containing up to six sugar units, a polyol and a betaine, said composition being free of potassium sorbate.

The invention also relates to an article comprising such a composition, and also to a cosmetic process for treating keratin materials by applying such a composition.

Due to the presence of water in these compositions, it is necessary to protect them against the growth and proliferation of microorganisms. This is because such a growth of microorganisms would rapidly make the compositions and/or the articles containing them unsuitable for use. To avoid this growth, it is especially necessary to protect the compositions against microorganisms capable of growing inside the composition and also against those which the user might introduce therein while handling it.

A composition comprising an aqueous medium and various compounds for protecting it against microorganisms, for instance organic acids such as potassium sorbate, is known.

However, the Applicant has demonstrated that such a composition comprising potassium sorbate does not have optimum stability properties. Specifically, a composition in the form of a cleansing gel containing 0.2% potassium sorbate undergoes an unfavorable change in stability after a few weeks spent at a temperature above 40° C., which is manifested by the appearance of yellowing of the composition.

The aim of the present invention is thus to provide a composition comprising water which has good stability, especially good microbiological stability, which is very well tolerated, with an esthetic appearance (such as the color) and which remains pleasant to the consumer, and which therefore does not have the drawbacks of the prior art.

The inventors have discovered that such a composition may be obtained by combining at least one monosaccharide or a polysaccharide containing up to six sugar units, a polyol and a betaine, more particularly by combining sucrose, 1,3-propanediol and cocoyl betaine, said composition being free of potassium sorbate. The inventors have discovered that a composition comprising, in an aqueous medium, at least one monosaccharide or a polysaccharide containing up to six sugar units, a polyol and a betaine, more particularly by combining sucrose, 1,3-propanediol and cocoyl betaine, said composition being free of potassium sorbate, has good stability, especially after storage for several weeks at a temperature above 40° C., in particular good microbiological stability, with an esthetic appearance, whose color remains pleasant to the consumer, while at the same time being very well tolerated.

One subject of the present invention is thus a composition comprising, in a physiologically acceptable aqueous medium, at least one monosaccharide or a polysaccharide containing up to six sugar units, a polyol and a betaine, said composition being free of potassium sorbate.

A subject of the present invention is more particularly a composition comprising, in a physiologically acceptable aqueous medium, sucrose, 1,3-propanediol and cocoyl betaine, said composition being free of potassium sorbate.

In the present invention, the contents are expressed as weight percentages of starting materials relative to the total weight of the composition, unless otherwise indicated.

The composition according to the invention comprises from 0% to 0.05% by weight, particularly from 0% to 0.01% by weight and more particularly from 0% to 0.001% by weight of potassium sorbate relative to the total weight of the composition. The composition according to the invention comprises less than 0.05% by weight, particularly less than 0.01% by weight and more particularly less than 0.001% by weight of potassium sorbate relative to the total weight of the composition. According to a preferred embodiment of the invention, the composition is free of potassium sorbate (zero content, or content equal to 0% by weight).

A monosaccharide or a polysaccharide containing up to six sugar units according to the invention is in pyranose and/or furanose form and of L and/or D series, said monosaccharide or polysaccharide bearing at least one hydroxyl function that is mandatorily free and/or optionally one or more amine functions that are mandatorily protected.

The preferred monosaccharides are chosen from D-glucose, D-fructose, D-galactose, D-mannose, D-xylose, D-lyxose, L-fucose, L-arabinose, L-rhamnose, D-glucoronic acid, D-galacturonic acid, D-iduronic acid, N-acetyl-D-glucosamine and N-acetyl-D-galactosamine, and advantageously denotes D-glucose, D-xylose, N-acetyl-D-glucosamine or L-fucose.

The preferred polysaccharides containing up to six sugar units are chosen from sucrose, D-maltose, D-lactose, D-cellobiose, D-maltotriose, a disaccharide combining a uronic acid chosen from D-iduronic acid and D-glucuronic acid with a hexosamine chosen from D-galactosamine, D-glucosamine, N-acetyl-D-galactosamine and N-acetyl-D-glucosamine, an oligosaccharide containing at least one xylose advantageously chosen from xylobiose, methyl-β-xylobioside, xylotriose, xylotetrose, xylopentose and xylohexose, and preferentially xylobiose, which is composed of two xylose molecules linked via a 1-4 bond. Advantageously, the composition comprises a polysaccharide, which is sucrose (also known as saccharose). By way of example, the sucrose is sold under the name CT Organic Sugar Golden Light® by the company Gebana or under the name Sucre Cristal Numéro 1 Pure Canne 1500® by the company Tereos.

The monosaccharide or a polysaccharide containing up to six sugar units, preferably sucrose, may be present in the composition in a content of between 3% and 20% by weight relative to the total weight of the composition, preferably in a content of between 4% and 15% by weight relative to the total weight of the composition, in particular in a content of between 5% and 10.5% by weight relative to the total weight of the composition, and particularly is present in a content of 5.5% by weight relative to the total weight of the composition.

According to the invention, the term "polyol" means a hydrocarbon-based chain comprising at least two carbon atoms, preferably from 2 to 50 carbon atoms, preferably from 4 to 20 carbon atoms, preferably containing from 2 to 10 carbon atoms and preferentially containing from 2 to 6 carbon atoms, and bearing at least two hydroxyl groups. The polyols used in the present invention may have a weight-average molecular mass of less than or equal to 1000 and preferably between 90 and 500.

More particularly, the polyol according to the invention may be chosen from glycerol, propylene glycol, butylene glycol, pentylene glycol, hexylene glycol, dipropylene glycol, diethylene glycol, 1,3-propanediol, D-mannitol (or 1,2,3,4,5,6-hexanehexol) and sorbitol (or D-glucitol), alone or as a mixture with other polyol glycol ethers (especially containing from 3 to 16 carbon atoms) such as mono-, di- or tripropylene glycol (C1-C4)alkyl ethers or mono-, di- or triethylene glycol (C1-C4)alkyl ethers. Advantageously, the polyol is 1,3-propanediol. By way of example, 1,3-propanediol is sold under the name Zemea Propanediol® by the company Dupont Tate and Lyle Bio Products.

The polyol, preferably 1,3-propanediol, may be present in the composition in a content of between 2% and 35% by weight relative to the total weight of the composition, in particular in a content of between 5% and 30% by weight relative to the total weight of the composition, particularly in a content of between 1% and 20% by weight relative to the total weight of the composition, more particularly in a content of between 2% and 15% by weight relative to the total weight of the composition, in particular in a content of between 2.5% and 10% by weight relative to the total weight of the composition, and is preferentially present in a content of 5% by weight relative to the total weight of the composition.

A betaine according to the invention is chosen from (C8-C20)alkyl betaines, sulfobetaines, (C8-C20)alkylsulfobetaines, (C8-C20)am idoalkyl(C1-C6)alkyl betaines and (C8-C20)amidoalkyl(C1-C6)alkylsulfobetaines, and is preferably cocoyl betaine, alone or as a mixture with other betaines.

Betaines that may especially be mentioned include alkyl betaines, for instance cocoyl betaine, such as the product sold under the name Dehyton AB-30® by the company Cognis, lauryl betaine, oxyethylenated (10 OE) lauryl betaine, such as the product sold under the name Lauryl Ether (10 OE) Betaine® by the company Shin Nihon Rica, or oxyethylenated (10 OE) stearyl betaine, such as the product sold under the name Stearyl Ether (10 OE) Betaine® by the company Shin Nihon Rica. Among the N-alkylamido betaines and derivatives thereof, examples that may be mentioned include the cocamidopropyl betaine sold under the name Lebon 2000 HG® by the company Sanyo or sold under the name Empigen BB® by the company Albright & Wilson, or the lauramidopropyl betaine sold under the name Rewoteric AMB12P® by the company Witco.

Mention may be made, as sultaines, of hydroxysultaines, such as cocamidopropyl hydroxysultaine, for instance the product sold under the name Rewoteric AM CAS by the company Goldschmidt-Degussa or the product sold under the name Crosultaine C-50® by the company Croda.

The betaine may be chosen from cetyl betaine, lauryl betaine, cocamidopropyl betaine and cocoyl betaine.

Preferably, the betaine is cocoyl betaine, or lauryl dimethylaminoacetic acid betaine (CAS No.: 68424-94-2). By way of example, the cocoyl betaine is sold under the name Dehyton AB 30® by the company Cognis (BASF), under the name Genagen KB® by the company Clariant, under the name Empigen BB/FL® by the company Huntsman, under the name Miratalne BB/FLA® by the company Rhodia, under the name Galaxy Coco Betaine® by the company Galaxy Surfactants, and under the name Tego Betaine AB1214® by the company Evonik Goldschmidt, in which the cocoyl betaine is present at an active material content of 30% in water and sodium chloride.

The betaine according to the invention, preferably cocoyl betaine, may be present in the composition in a content of between 0.01% and 5% by weight relative to the total weight of the composition, in particular in a content of between 0.05% and 1% by weight relative to the total weight of the composition, and particularly in a content of 0.5% by weight relative to the total weight of the composition.

Advantageously, the composition according to the invention as defined above comprises sucrose, 1,3-propanediol and cocoyl betaine.

The betaine according to the invention, preferably cocoyl betaine, may be present in the composition in a content of between 0.003% and 1.5% by weight of active material relative to the total weight of the composition, in particular in a content of between 0.015% and 0.33% by weight of active material relative to the total weight of the composition, and particularly in a content of 0.15% by weight of active material relative to the total weight of the composition.

Advantageously, the composition according to the invention as defined above comprises sucrose, 1,3-propanediol and cocoyl betaine, while being free of potassium sorbate.

Preferably, the composition according to the invention, free of potassium sorbate, comprises, in an aqueous medium, sucrose in a content ranging from 5% to 10.5% by weight relative to the total weight of the composition, 1,3-propanediol in a content ranging from 2.5% to 10% by weight and cocoyl betaine in a content ranging from 0.05% to 1% by weight relative to the total weight of the composition.

Preferably, the composition according to the invention, free of potassium sorbate, comprises, in an aqueous medium, sucrose in a content ranging from 5% to 10.5% by weight relative to the total weight of the composition, 1,3-propanediol in a content ranging from 2.5% to 10% by weight and cocoyl betaine in a content ranging from 0.015% to 0.3% by weight of active material relative to the total weight of the composition.

More particularly, the composition according to the invention, free of potassium sorbate, comprises, in an aqueous medium, sucrose in a content ranging from 5% to 10.5% by weight relative to the total weight of the composition, 1,3-propanediol in a content ranging from 2.5% to 10% by weight and cocoyl betaine in a content of 0.5% by weight relative to the total weight of the composition.

More particularly, the composition according to the invention, free of potassium sorbate, comprises, in an aqueous medium, sucrose in a content ranging from 5% to 10.5% by weight relative to the total weight of the composition, 1,3-propanediol in a content ranging from 2.5% to 10% by weight and cocoyl betaine in a content of 0.15% by weight of active material relative to the total weight of the composition.

The composition according to the invention comprises an aqueous medium.

The composition may comprise water present in a content of between 60% and 95% by weight, preferably in a content of between 65% and 90% by weight and preferentially in a content of between 70% and 85% by weight relative to the total weight of the composition.

The composition according to the invention generally has a pH preferably ranging from 3 to 9, preferentially from 4 to 8 and preferentially from 4 to 6.5.

The composition according to the invention may comprise from 0 to 1% by weight of oil, and/or one or more additional surfactants in a content of between 0 and 8% by weight, preferably between 0 and 5% and particularly from 0.05% to 3% by weight relative to the total weight of the composition.

According to a preferred embodiment of the invention, the composition is free of oil (zero content) and/or is free of additional surfactants. The term "additional surfactants" means a surfactant other than a monosaccharide or a polysaccharide containing up to six sugar units, a polyol and a betaine according to the invention as defined above.

Nonionic, anionic, amphoteric or zwitterionic surfactants that promote the removal of makeup and impurities, and which can make the composition foaming, may also be added to the composition of the invention. They may especially be foaming surfactants. Examples of surfactants of this type that may be mentioned include:

(1) among the nonionic surfactants, oxyethylenated oxypropylenated block polymers such as Poloxamer 184 (CTFA name); alkylpolyglycosides and especially alkylpolyglucosides (APGs) bearing an alkyl group comprising from 6 to 30 carbon atoms (C6-C30-alkyl polyglucosides) and preferably 8 to 16 carbon atoms, for instance decyl glucoside (Alkyl-C9/C11-polyglucoside (1.4)), such as the product sold under the name Mydol 10 by the company Kao Chemicals, the product sold under the name Plantaren 2000 UP or Plantacare 2000 UP by the company Henkel, and the product sold under the name Oramix NS 10 by the company SEPPIC; caprylyl/capryl glucoside, such as the product sold under the name Oramix CG 110 by the company SEPPIC; lauryl glucoside, such as the products sold under the names Plantaren 1200 N and Plantacare 1200 by the company Henkel; and cocoyl glucoside, such as the product sold under the name Plantacare 818/UP by the company Henkel;

(2) among the anionic surfactants, alkyl sulfates, alkyl ether sulfates and salts thereof, especially the sodium salts thereof, for instance the mixture of sodium laureth sulfate/magnesium laureth sulfate/sodium laureth-8 sulfate/magnesium laureth-8 sulfate sold under the name Texapon ASV by the company Henkel; sodium lauryl ether sulfate (70/30 C12-14) (2.2 OE) sold under the names Sipon AOS 225 or Texapon N702 Pate by the company Henkel, ammonium lauryl ether sulfate (70/30 C12-14) (3 OE) sold under the name Sipon LEA 370 by the company Henkel; ammonium (C12-C14) alkyl ether (9 OE) sulfate sold under the name Rhodapex AB/20 by the company Rhodia Chimie;

(3) among the amphoteric or zwitterionic surfactants, alkylamido alkylamine derivatives such as N-disodium N-cocoyl-N-carboxymethoxyethyl-N-carboxymethylethylenediamine (CTFA name: Disodium cocoamphodiacetate) sold as an aqueous saline solution under the name Miranol C2M Conc NP by the company Rhodia Chimie; N-sodium N-cocoyl-N-hydroxyethyl-N-carboxymethylethylenediamine (CTFA name: sodium cocamphoacetate) and the mixture of coconut acid ethanolam ides (CTFA name: Cocamide DEA).

The composition may also comprise a mixture of these surfactants.

The oil may be a volatile oil, especially chosen from volatile silicone oils and volatile nonsilicone oils.

The term "volatile oil" means any nonaqueous medium that is capable of evaporating from the skin or the lips in less than one hour, and especially having a vapor pressure, at room temperature and atmospheric pressure, ranging from $10^{-3}$ to 300 mmHg (0.13 Pa to 40 000 Pa).

As volatile oils that can be used in the invention, use may be made of volatile nonsilicone oils, especially $C_8$-$C_{16}$ isoparaffins, for instance isododecane, isodecane, isohexadecane and, for example, the oils sold under the trade names Isopar and Permethyl, and especially isododecane (Permethyl 99 A).

As volatile silicone oils that can be used in the invention, mention may be made of linear or cyclic silicones containing from 2 to 7 silicon atoms, these silicones optionally comprising alkyl or alkoxy groups containing from 1 to 10 carbon atoms. In particular, mention may be made of octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane and decamethyltetrasiloxane, and mixtures thereof.

The oil may also be a nonvolatile oil.

The term "nonvolatile oil" means an oil that is capable of remaining on the skin at room temperature (25° C.) and atmospheric pressure for at least one hour, and especially having a nonzero vapor pressure at room temperature (25° C.) and atmospheric pressure, of less than 0.01 mmHg (1.33 Pa).

As nonvolatile oils that may be used in the invention, mention may be made of:

nonvolatile nonsilicone and especially hydrocarbon-based oils, such as liquid paraffin (or petroleum jelly), squalane, hydrogenated polyisobutylene (Parleam oil), perhydrosqualene, mink oil, turtle oil, soybean oil, sweet almond oil, beauty-leaf oil, palm oil, grapeseed oil, sesame oil, corn oil, arara oil, rapeseed oil, sunflower oil, cotton oil, apricot oil, castor oil, avocado oil, jojoba oil, olive oil or cereal germ oil; esters of lanolic acid, of oleic acid, of lauric acid or of stearic acid; esters derived from long-chain acids or alcohols (i.e. containing from 6 to 20 carbon atoms), especially the esters of formula RCOOR' in which R represents a higher fatty acid residue comprising from 7 to 19 carbon atoms and R' represents a hydrocarbon-based chain comprising from 3 to 20 carbon atoms, in particular C12-C36 esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl) succinate, diisostearyl malate, and glyceryl or diglyceryl triisostearate; higher fatty acids, especially of C14-C22, such as myristic acid, palmitic acid, stearic acid, behenic acid, oleic acid, linoleic acid, linolenic acid or isostearic acid; higher fatty alcohols, especially of C16-C22, such as cetanol, oleyl alcohol, linoleyl alcohol or linolenyl alcohol, isostearyl alcohol or octyldodecanol; and mixtures thereof.

nonvolatile silicone oils such as nonvolatile polydimethylsiloxanes (PDMSs); polydimethylsiloxanes comprising alkyl, alkoxy or phenyl groups, pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones and diphenylmethyldiphenyltrisiloxanes; polysiloxanes modified with fatty acids (especially of C8-C20), fatty alcohols (especially of C8-C20) or polyoxyalkylenes (especially polyoxyethylene and/or polyoxypropylene); amino silicones; silicones containing hydroxyl groups; fluoro silicones comprising a fluoro group that is pendent or at the end of a silicone chain, containing from 1 to 12 carbon atoms, some or all of the hydrogens of which are replaced with fluorine atoms; and mixtures thereof.

The composition according to the invention may also comprise a sequestrant. Such a sequestrant may be chosen from sodium phytate, EDTA, ascorbic acid, tartaric acid, galactaric acid, gluconolactone and sodium hexametaphosphate. The sequestrant may especially be in a content ranging from 0.01% to 0.5% by weight relative to the total weight of the composition and preferably ranging from 0.1% to 0.2% by weight relative to the total weight of the composition.

The composition may comprise fillers in a content of less than or equal to 3% by weight, relative to the total weight of the composition, especially in a content ranging from 0.1% to 3% by weight. According to one embodiment of the invention, the composition is free of fillers (zero content).

The term "filler" means any colorless or colored particle chosen from lamellar, spherical or oblong mineral or organic fillers, which is chemically inert in the composition.

Mention may be made of talc, mica, silica, kaolin, laponite, polyamide powders such as Nylon®, poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie), acrylic polymer particles, especially of acrylic acid copolymer, for instance Polytrap® (Dow Corning), polyurethane powders, silicone resin microbeads (for example Tospearls® from Toshiba), precipitated calcium carbonate, dicalcium phosphate, magnesium carbonate, magnesium hydrocarbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate, and mixtures thereof.

The composition according to the invention may comprise hydrophilic or lipophilic gelling agents, especially in a weight content preferentially from 0.01% to 0.5% by weight relative to the total weight of the composition.

As hydrophilic gelling agents that may be used in the invention, mention may be made of carboxyvinyl polymers (carbomer), acrylic copolymers such as acrylate/alkyl acrylate copolymers, polyacrylamides, polysaccharides such as hydroxypropylcellulose, natural gums, and clays, and, as lipophilic gelling agents, mention may be made of modified clays such as bentones, metal salts of fatty acids, for instance aluminum stearates, and hydrophobic silica, ethylcellulose and polyethylene.

The composition advantageously comprises a cosmetic or dermatological active agent, preferably a hydrophilic cosmetic active agent. The hydrophilic active agent may be any water-soluble molecule with cosmetic or dermatological activity, and having a solubility in water of at least 0.25% by weight at room temperature (25° C.).

The hydrophilic active agents may be chosen especially from moisturizing, calmative, antiaging, matting, muscle-relaxant, decongestant, blemish-removing, depigmenting and bleaching active agents.

The hydrophilic active agent(s) may be present in the composition according to the invention in a content ranging from 0.001% to 10% by weight, preferably ranging from 0.01% to 5% by weight and preferentially ranging from 0.05% to 1% by weight relative to the total weight of the composition.

The composition according to the invention may also comprise adjuvants that are common in cosmetics and dermatology, such as antioxidants, fragrances, pigments, UV-screening agents, odor absorbers, dyestuffs, conditioning agents, propellants and opacifiers. The amounts of these various adjuvants are those conventionally used in the fields under consideration, for example from 0.01% to 20% of the total weight of the composition.

Needless to say, a person skilled in the art will take care to select the optional compound(s) to be added to the compositions according to the invention and also the concentration thereof, such that the advantageous properties intrinsically associated with the compositions in accordance with the invention are not, or are not substantially, adversely affected by the envisaged addition.

Preferably, the composition according to the invention is in the form of a solution, in the form of a lotion, in the form of an aqueous or aqueous-alcoholic gel, in the form of an aqueous base of a two-phase formulation, or in the form of a sprayable aerosol composition.

The composition may be a care composition, especially a care product for keratin materials, such as the skin, a care base for the skin or the scalp, a face or scalp lotion, a care gel (day, night or antiwrinkle care), a makeup or makeup-removing or treating base; a lipcare composition (lip balm); an antisun or self-tanning composition; a cleansing body hygiene composition such as a shower gel, a shampoo or a deodorant; an after-shave gel or lotion, a milk, or, preferably, a fluid for wipes.

The composition of the invention can be a cosmetic or dermatological composition. Preferentially, according to the invention, the composition is a cosmetic composition and even more preferentially a cosmetic composition for topical application.

The term "cosmetic composition" is intended to mean a substance or a preparation intended to be brought into contact with the various superficial parts of the human body, in particular the epidermis, the bodily-hair and head-hair systems, the nails, the lips and the oral mucous membranes, with a view, exclusively or mainly, to cleansing them, making them more attractive, fragrancing them, modifying their appearance, protecting them, keeping them in good condition, or correcting body odors.

For the purposes of the present invention, the term "physiologically acceptable medium" is intended to mean a medium that is suitable for the topical administration of a composition, and that is compatible with all human keratin materials, such as the skin, the lips, the nails, the mucous membranes, the eyelashes, the eyebrows, the scalp and/or the hair, or any other area of bodily skin.

According to the invention, a physiologically acceptable medium is preferentially a cosmetically acceptable medium, that is to say a medium which is devoid of unpleasant odor or appearance and which is entirely compatible with the topical administration route.

More particularly, the composition according to the invention is intended to be administered topically, that is to say by application to the surface of the keratin material under consideration, such as the skin under consideration.

The term "keratin materials" according to the invention is intended to mean the skin, of the body, face and/or area around the eyes, the lips, the nails, the mucous membranes, the eyelashes, the eyebrows, body hair, the scalp and/or the hair, or any other area of bodily skin. More particularly, the keratin materials according to the invention are the scalp, the hair and/or the skin.

Preferably, the keratin materials according to the invention are the scalp and/or the hair.

Preferably, the keratin materials according to the invention are the skin.

The term "skin" is intended to mean all of the skin of the body, and, in a particular embodiment, the skin of the face, neckline, neck, arms and forearms, or even more preferably still the skin of the face, in particular of the forehead, nose, cheeks, chin and area around the eyes.

Another subject of the present invention is an article comprising a/ a water-insoluble substrate, and b/ a composition according to the invention as defined above, added to or impregnated onto said substrate a/.

Preferably, the present invention relates to an article comprising a/ a water-insoluble substrate, and b/ a composition comprising, in a physiologically acceptable aqueous medium, sucrose, 1,3-propanediol and cocoyl betaine, said composition being free of potassium sorbate, which is added to or impregnated onto said substrate a/.

This article may especially constitute an article that is suitable for caring for, cleansing and/or removing makeup from keratin materials, such as the skin, and especially an article for cleansing or removing makeup from facial and/or bodily skin, and/or an article for cleansing or removing makeup from the eyes.

This article may especially be a patch, a wipe, a pad, a mask or any type of woven or nonwoven support.

The composition according to the invention may be impregnated into or added to a woven or nonwoven article as defined above.

The water-insoluble substrate (a/) may be chosen from the group comprising woven materials, nonwoven materials, foams, sponges or wadding, as sheets, balls or films. It may especially be a nonwoven substrate based on fibers of natural origin (flax, wool, cotton or silk) or of synthetic origin (cellulose derivatives, viscose, polyvinyl derivatives, polyesters such as polyethylene terephthalate, polyolefins such as polyethylene or polypropylene, polyamides such as Nylon, or acrylic derivatives). Nonwovens are described in general in Riedel's *Nonwoven Bonding Methods & Materials*, Nonwoven World (1987). These substrates are obtained according to the usual processes of the art for preparing nonwovens.

According to a particular embodiment of the invention, the insoluble substrate may contain at least one of the compounds according to the invention chosen from a monosaccharide or a polysaccharide containing up to six sugar units, a polyol and a betaine, optionally attached to the support via known means for grafting biocidal agents onto fibers.

This substrate may comprise one or more layers with identical or different properties and having elasticity and softness properties and other properties that are suited to the desired use. The substrates may comprise, for example, two parts having different elasticity properties as described in document WO-A-99/13861 or may comprise only one layer with different densities as described in document WO-A-99/25318 or may comprise two layers with different textures as described in document WO-A-98/18441.

The substrate may have any size and any shape that are suitable for the desired aim.

It generally has a surface area between 0.005 $m^2$ and 0.1 $m^2$ and preferably between 0.01 $m^2$ and 0.05 $m^2$. It is preferably in the form of rectangular wipes or circular compresses.

The final article comprising the substrate and the impregnation composition is generally moist, with a degree of impregnation with the composition ranging, for example, from 200% to 1000% and preferably from 250% to 350% by weight of composition relative to the weight of substrate. The techniques for impregnating substrates with compositions are well known in this field and are all applicable to the present invention. In general, the impregnation composition is added to the substrate via one or more techniques comprising immersion, coating, vaporization, etc.

It is also possible to make an article (especially a wipe) offered in dry form, either by removing the water from the composition after it has been impregnated onto the substrate, or by impregnating the substrate with a composition in dry form as a powder, granules or film, via any known preparation means such as the welding and bonding of multilayers via thermal or ultrasonic routes. In the latter embodiment, the composition is dried by any known means: atomization, lyophilization or another similar process.

Moist wipes or dry wipes may thus be obtained according to the intended use. The moist wipes may be used as obtained, whereas the dry wipes are moistened before use.

A subject of the present invention is also the cosmetic use of a composition as above, characterized in that said composition is applied to keratin materials, such as the skin and/or the hair, for caring for, cleansing and/or removing makeup from said keratin materials.

A subject of the present invention is also the cosmetic use of an article as defined above, characterized in that said article, in which is impregnated or added a composition according to the invention as defined above, is passed onto keratin materials.

A subject of the present invention is also a cosmetic process for treating keratin materials, in which a composition as defined above is applied, or in which an article as defined above is passed onto said keratin material(s).

The cosmetic treatment process is more particularly a cosmetic treatment process for caring for, cleansing and/or removing makeup from keratin materials.

Preferably, the keratin materials according to the invention are the skin.

Throughout the text hereinbelow, the percentages are given on a weight basis, unless otherwise mentioned.

The examples that follow illustrate the invention, and are given purely as nonlimiting illustrations.

The terms "between . . . and . . . " and "ranging from . . . to . . . " should be understood as being inclusive of the limits, unless otherwise specified.

The examples and figures that follow are presented as nonlimiting illustrations of the invention. The compounds are, depending on the case, cited as the chemical names or as the CTFA names (*International Cosmetic Ingredient Dictionary and Handbook*).

In these examples, the amounts of the composition ingredients are given as weight percentages relative to the total weight of the composition.

EXAMPLE 1

Compositions According to the Invention in the Form of a Lotion for Caring for/or Cleansing/or Removing Makeup from the Skin by Topical Application The percentages are expressed as weight percentages relative to the total weight of the compositions.

The process for obtaining these compositions prepared in a lotion form comprises various steps:

A) mixing xanthan gum in 1,3-propanediol in order to fully disperse the latter. Adding this preparation to part of the water, for gelation, in a deflocculator.

B) mixing with magnetic stirring of the remaining water, the sucrose, the sodium phytate and the glycerol until the starting materials have dissolved.

C) mixing phases A and B with magnetic stirring.
D) adding cocoyl betaine.
E) adjusting the pH with a preparation of citric acid dissolved in water.

|  | Composition 1 according to the invention in the form of a makeup-removing lotion | Composition 2 according to the invention in the form of a fluid for wipes | Composition 3 according to the invention in the form of a facial cleanser |
|---|---|---|---|
| Citric acid | for pH adjustment to $5 \pm 0.5$ | for pH adjustment to $5 \pm 0.5$ | for pH adjustment to $5 \pm 0.5$ |
| Sucrose | 5.5 | 10 | 5.5 |
| Disodium EDTA |  |  |  |
| Sodium phytate | 0.15 | 0.15 | 0.15 |
| Xanthan gum | 0.1 | 0.1 | 0.1 |
| Glycerol | 7 | 7 | 7 |
| 1,3-Propanediol | 5 | 2.6 | 5 |
| Water | qs 100 | qs 100 | qs 100 |
| Disodium cocoamphodiacetate |  |  | 0.5 |
| Cocoyl betaine (Dehyton AB 30 ® from the company Cognis (BASF) containing 30% active material) | 0.5 | 0.5 | 0.5 |
| Poloxamer 184 |  |  | 2 |
| Niacinamide |  | 0.15 |  |

EXAMPLE 2

Evaluation of the Stability of the Compositions According to the Invention, and Measurement of the Stability of the Microbiological Protection The following test demonstrates the activity of the combination according to the invention on microorganisms.

The method of the challenge test consists of an artificial contamination of the sample with microbial strains from collection (bacteria, yeasts and molds) and of an evaluation of the number of revivable microorganisms seven days after inoculation.

A test (Challenge Test) is performed on cosmetic formulations.

The antimicrobial activity of a cosmetic formula according to the invention, free of potassium sorbate, and containing, respectively, cocoyl betaine in various contents (0.5% or 1% by weight relative to the total weight of the composition), sucrose in various contents (5%, 5.5% or 10% by weight) and 1,3-propanediol in various contents (2.6%, 5% or 10% by weight) was compared with the same formula alone (Control), after inoculation of about $10^6$ cfu (colony-forming units)/gram of cosmetic product.

5 pure cultures of microorganisms are used.

| MICROORGANISMS | SUBCULTURING MEDIUM | T° | ATCC |
|---|---|---|---|
| Escherichia coli (Ec) | Trypto-casein soy | 35° C. | 8739 |
| Staphylococcus aureus | Trypto-casein soy | 35° C. | 6538 |
| Enterococcus faecalis (Ef) | Trypto-casein soy | 35° C. | 33186 |
| Pseudomonas aeruginosa (Pa) | Trypto-casein soy | 35° C. | 19429 |
| Candida albicans (Ca) | Sabouraud | 35° C. | 10231 |
| Aspergillus niger (An) | Malt | 35° C. | 6275 |

ATCC = American Type Culture Collection

The strains of gram—bacteria (*Escherichia coli* and *Pseudomonas aeruginosa*), gram +bacteria (*Enterococcus faecalis, Staphylococcus aureus*), yeast (*Candida albicans*), and mold (*Aspergillus niger*) are inoculated into subculturing medium, respectively the day before inoculation for the bacteria and the yeast, and 5 days before inoculation for the mold.

On the day of inoculation:
  a suspension in tryptone salt diluent is prepared, respectively, for the bacteria and the yeast, so as to obtain by spectrophotometer a suspension with an optical density of between 35% and 45% of transmitted light at 544 nm;
  for the mold, the spores are collected by washing the agar with 6 to 7 ml of harvesting solution and the suspension is recovered in a sterile tube or flask.

After having homogenized the microbial suspension, 0.2 ml of inoculum (the suspensions are used pure: between $1 \times 10^8$ and $3 \times 10^8$ colony-forming units (cfu) per ml) are placed in each pill bottle and the microbial suspension is completely homogenized in the 20 g of product (aqueous solution containing the three compounds according to the invention at the concentrations indicated) using a spatula.

The content of microorganisms present in the product corresponds after homogenization to a concentration of $10^6$ microorganisms per gram of product, i.e. inoculation to 1% of an inoculum containing $10^8$ microorganisms per ml.

After 7 days of contact time between the microorganisms and the product at 22° C.±2° C. and in the dark, ten-fold dilutions are carried out and the number of revivable microorganisms remaining in the product is counted.

The logarithmic decrease of the number of microorganisms after 7, 14 and 28 days is then calculated.

The percentages are expressed as weight percentages relative to the total weight of the formulae.

|  | Formula A (weight %) according to the invention | Formula B (weight %) | Formula C (weight %) |
|---|---|---|---|
| Citric acid | adjustment of the pH to $5 \pm 0.5$ | adjustment of the pH to $5 \pm 0.5$ | adjustment of the pH to $5 \pm 0.5$ |
| Sucrose | 5 | 5 |  |
| Potassium sorbate |  | 0.2 |  |
| Xanthan gum | 0.1 | 0.1 | 0.1 |
| Glycerol | 7 | 7 | 7 |
| 1,3-Propanediol | 10 | 10 |  |

-continued

|  |  |  |  |  |  |
|---|---|---|---|---|---|
|  | Water | qs 100 | qs 100 | qs 100 |  |
|  | Cocoyl betaine (Dehyton AB 30 ® from the company Cognis (BASF) containing 30% active material) | 1 | 1 |  |  |
| Stability after several weeks at 40° C. | appearance/color pH | NTR stable | yellowing stable | cloudiness | standards ISO 11930: criterion A |
| challenge test results | bacteria | 7 days: reduction > 4 log 14 days: reduction > 4 log 28 days: reduction > 4 log | 7 days: reduction > 4 log 14 days: reduction > 4 log 28 days: reduction > 4 log | 7 days: increase log 14 days: increase log 28 days: increase log | 7 days: reduction > 3 log 14 days: reduction > 3 log 28 days: reduction > 3 log |
|  | yeasts | 7 days: reduction > 4 log 14 days: reduction > 4 log 28 days: reduction > 4 log | 7 days: reduction > 4 log 14 days: reduction > 4 log 28 days: reduction > 4 log | 7 days: increase log 14 days: increase log | 7 days: reduction > 1 log 14 days: reduction > 1 log 28 days: reduction > 1 log |
|  | molds | 7 days: reduction > 2 log 14 days: reduction > 3 log 28 days: reduction > 4 log | 7 days: reduction > 4 log 14 days: reduction > 4 log 28 days: reduction > 4 log | 7 days: increase log 14 days: increase log 28 days: increase log | 14 days: reduction > 0 log 28 days: reduction > 1 log |

The results of the study presented in the preceding table show, surprisingly, that the combination according to the invention comprising sucrose, 1,3-propanediol and cocoyl betaine, and being free of potassium sorbate, in a simple base (formula A) shows good microbiological protection, with an esthetic appearance, including an esthetic color, and is stable for several weeks at 40° C., and which does not have the drawback of yellowing after several weeks at 40° C., unlike the formula comprising in the same simple base a combination of these three ingredients but with potassium sorbate (formula B).

|  |  | Composition 1 according to the invention in the form of a makeup-removing lotion of Example 1 | Composition 2 according to the invention in the form of a fluid for wipes of Example 1 | Composition 3 according to the invention in the form of a facial cleanser of Example 1 |  |
|---|---|---|---|---|---|
| Stability after several weeks at 40° C. | appearance/color pH | NTR stable | NTR stable | NTR stable | standards ISO 11930: criterion A |
| challenge test results | bacteria | 7 days: reduction > 4 log 14 days: reduction > 4 log 28 days: reduction > 4 log | 7 days: reduction > 4 log 14 days: reduction > 4 log 28 days: reduction > 4 log | 7 days: reduction > 4 log 14 days: reduction > 4 log 28 days: reduction > 4 log | 7 days: reduction > 3 log 14 days: reduction > 3 log 28 days: reduction > 3 log |
|  | yeasts | 7 days: reduction > 4 log 14 days: reduction > 4 log 28 days: reduction > 4 log | 7 days: reduction > 4 log 14 days: reduction > 4 log 28 days: reduction > 4 log | 7 days: reduction > 4 log 14 days: reduction > 4 log 28 days: reduction > 4 log | 7 days: reduction > 1 log 14 days: reduction > 1 log 28 days: reduction > 1 log |

| | Composition 1 according to the invention in the form of a makeup-removing lotion of Example 1 | Composition 2 according to the invention in the form of a fluid for wipes of Example 1 | Composition 3 according to the invention in the form of a facial cleanser of Example 1 | |
|---|---|---|---|---|
| molds | 7 days: reduction > 2 log 14 days: reduction > 3 log 28 days: reduction > 4 log | 7 days: reduction > 2 log 14 days: reduction > 3 log 28 days: reduction > 4 log | 7 days: reduction > 2 log 14 days: reduction > 2 log 28 days: reduction > 2 log | 14 days: reduction > 0 log 28 days: reduction > 1 log |

This second study, the results of which are presented in the preceding table, demonstrates that compositions (Compositions 1, 2 and 3) according to the invention comprising in an aqueous medium sucrose, 1,3-propanediol and cocoyl betaine, and free of potassium sorbate, show good microbiological stability over time, have an esthetic appearance, including an esthetic color, and are stable after several weeks at 40° C. The combination of sucrose, 1,3-propanediol and cocoyl betaine has a very broad antimicrobial spectrum due to its antibacterial and antifungal activity.

The invention claimed is:

1. A composition comprising, in a physiologically acceptable aqueous medium, at least one monosaccharide or a polysaccharide containing up to six sugar units in an amount of between 3% and 20% by weight relative to the total weight of the composition, 1,3-propanediol and a betaine in an amount of between 0.015% and 1.5% by weight relative to the total weight of the composition, said composition being free of potassium sorbate.

2. The composition as claimed in claim 1 wherein the monosaccharide is chosen from D-glucose, D-galactose, D-mannose, D-fructose, D-xylose, D-lyxose, L-fucose, L-arabinose, L-rhamnose, D-glucuronic acid, D-galacturonic acid, D-iduronic acid, N-acetyl-D-glucosamine and N-acetyl-D-galactosamine.

3. The composition as claimed in claim 1, wherein the betaine is chosen from (C8-C20)alkyl betaines, sulfobetaines, (C8-C20)alkylsulfobetaines, and(C8-C20)alkylamido(C1-C6)alkyl betaines.

4. The composition as claimed in claim 1, which comprises sucrose, 1,3-propanediol and cocoyl betaine.

5. The composition as claimed in claim 1, which comprises water present in a content of between 60% and 95% by weight relative to the total weight of the composition.

6. The composition as claimed in in claim 1, wherein said monosaccharide or polysaccharide is present in a content of between 5% and 10.5% by weight relative to the total weight of the composition.

7. The composition as claimed in claim 1, wherein said 1,3-propanediol, is present in a content of between 2% and 35% by weight relative to the total weight of the composition.

8. The composition as claimed in in claim 1, which comprises one or more oils in a content of between 0 and 1% by weight, and/or one or more additional surfactants in a content of between 0 and 8% by weight relative to the total weight of the composition.

9. The composition as claimed in claim 1, wherein said composition is a cosmetic composition.

10. The composition as claimed in in claim 1, wherein said composition is in the form of a solution, an aqueous gel or an aqueous-alcoholic gel.

11. An article comprising
a/a water-insoluble substrate, and
b/a composition as defined in in claim 1, being , added to or impregnated onto said substrate a/.

12. The article as claimed in claim 11, which is in the form of rectangular wipes or of circular compresses.

13. A cosmetic process for treating keratin materials in which a composition comprising, in a physiologically acceptable aqueous medium, at least one monosaccharide or a polysaccharide containing up to six sugar units in an amount of between 3% and 20% by weight relative to the total weight of the composition, 1,3-propanediol and a betaine in an amount of between 0.015% and 1.5% by weight relative to the total weight of the composition, said composition being free of potassium sorbate is applied, or in which an article as defined in claim 11 is passed onto said keratin material(s).

14. The composition as claimed in claim 1 wherein said betaine is present in an amount of between 0.015% and 0.33% by weight of active material relative to the total weight of the composition.

15. The composition as claimed in claim 1 wherein said betaine is cocoyl betaine.

16. The composition as claimed in claim 2, wherein the betaine is chosen from (C8-C20)alkyl betaines, sulfobetaines, (C8-C20)alkylsulfobetaines, and (C8-C20)alkylamido(C1-C6)alkyl betaines.

17. The composition as claimed in claim 2, which comprises water present in a content of between 60% and 95% by weight.

18. The composition as claimed in claim 3, which comprises water present in a content of between 60% and 95% by weight.

19. The composition as claimed in claim 4, which comprises water present in a content of between 60% and 95% by weight.

20. The composition as claimed in claim 2, wherein said monosaccharide or polysaccharide is present in a content of between 5% and 10.5% by weight relative to the total weight of the composition.

21. The composition as claimed in claim 1 wherein the polysaccharide is chosen from D-glucose, D-xylose, N-acetyl-D-glucosamine or L-fucose, D-maltose, D-lactose, D-cellobiose and sucrose.

* * * * *